(12) United States Patent
New

(10) Patent No.: US 7,651,995 B2
(45) Date of Patent: *Jan. 26, 2010

(54) ABSORPTION ENHANCERS SUCH AS E.G. BHT, BHA OR PROPYL GALLATE

(75) Inventor: Roger R. C. New, London (GB)

(73) Assignee: Axcess Limited, St. Helier, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/553,324

(22) PCT Filed: Apr. 15, 2004

(86) PCT No.: PCT/GB2004/001650

§ 371 (c)(1),
(2), (4) Date: Oct. 17, 2005

(87) PCT Pub. No.: WO2004/091584

PCT Pub. Date: Oct. 28, 2004

(65) Prior Publication Data

US 2006/0223740 A1   Oct. 5, 2006

(30) Foreign Application Priority Data

Apr. 15, 2003   (GB) ................. 0308732.7

(51) Int. Cl.
*A61K 38/28* (2006.01)
*A61K 38/02* (2006.01)
(52) U.S. Cl. ................ 514/3; 514/2; 424/1.69
(58) Field of Classification Search ........ None
See application file for complete search history.

(56) References Cited

U.S. PATENT DOCUMENTS

| | | | |
|---|---|---|---|
| 3,996,355 A | 12/1976 | Lin et al. | |
| 4,789,660 A | 12/1988 | Enever et al. | |
| 5,206,219 A | 4/1993 | Desai | |
| 5,342,625 A | 8/1994 | Hauer et al. | |
| 5,645,856 A | 7/1997 | Lacy et al. | |
| 5,653,987 A | 8/1997 | Modi et al. | |
| 5,756,450 A | 5/1998 | Hahn et al. | |
| 5,849,700 A | 12/1998 | Sorensen et al. | |
| 5,849,704 A | 12/1998 | Sorensen et al. | |
| 5,853,748 A * | 12/1998 | New ................. | 424/439 |
| 5,891,671 A | 4/1999 | Suzuki et al. | |
| 5,962,522 A * | 10/1999 | Wacher et al. ........... | 514/544 |
| 6,180,666 B1 * | 1/2001 | Wacher et al. ........... | 514/544 |
| 6,342,249 B1 * | 1/2002 | Wong et al. ............. | 424/473 |
| 6,358,924 B1 | 3/2002 | Hoffmann | |
| 7,446,091 B2 | 11/2008 | Van Den Berghe | |
| 7,491,187 B2 | 2/2009 | Van Den Berghe et al. | |
| 2001/0014675 A1 | 8/2001 | Loria | |
| 2003/0069170 A1 | 4/2003 | Soltero et al. | |
| 2006/0122097 A1 | 6/2006 | New et al. | |
| 2006/0223740 A1 | 10/2006 | New | |

FOREIGN PATENT DOCUMENTS

| | | |
|---|---|---|
| EP | 0 127 535 | 12/1984 |
| EP | 0 295 941 | 12/1988 |
| EP | 0 371 010 A1 | 5/1990 |
| GB | 354184 | 7/1931 |
| JP | 52-057313 A | 11/1975 |
| JP | 56138168 A | 10/1981 |
| JP | 5-246846 | 9/1993 |
| WO | 93/06854 | 4/1993 |
| WO | 96/40192 | 12/1996 |
| WO | 97/21448 | 6/1997 |
| WO | 97/33531 | 9/1997 |
| WO | WO 99/29336 | 6/1999 |
| WO | WO 00/22909 | 4/2000 |
| WO | WO 01/74169 A1 | 10/2001 |
| WO | WO 0222158 * | 3/2002 |
| WO | 02/28436 A1 | 4/2002 |
| WO | WO 02/28436 * | 4/2002 |

(Continued)

OTHER PUBLICATIONS

Ivanovic et al. "Effect of pH on the Retention Behavior of Some Preservatives-Antioxidants in Reversed-Phase High-Performance Liquid Chromatography", 1995, Chromatographia, vol. 40. pp. 652-656.*
Read et al. "Antisense Strategies and Non-Viral Gene Therapy for Cancer", 2002, Expert Opin. Ther. Patents, vol. 12. pp. 379-391.*
Bradley, C., "The glitazones: a new treatment for type 2 diabetes mellitus." Int. Crit. Care Nurs. 2002, 18, 189-91.
Strickley, R.G., Anderson, B.D., "Solid-State Stability of Human Insulin II. Effect of Water on Reactive Intermediate Partitioning in Lyophiles from pH 2-5 Solutions: Stabilization against Covalent Dimer Formation", J. Pharm. Sci. 1997, 86 (6), 645-53.
Harsch et al, "Syringe, pen, inhaler—the evolution of insulin therapy". Med. Sci. Monit. 2001, 7(4), 833-836.

(Continued)

*Primary Examiner*—Maury Audet
(74) *Attorney, Agent, or Firm*—Nixon & Vanderhye P.C.

(57) ABSTRACT

The invention provides a pharmaceutical composition comprising a mixture of (a) an active macromolecular principle, and (b) an aromatic alcohol absorption enhancer chosen from butylated hydroxy toluene, butylated hydroxy anisole and analogues and derivatives thereof, wherein the aromatic alcohol absorption enhancer is present in an amount by weight greater than or equal to that of the active macromolecular principle, and further comprises a pharmaceutical composition comprising a mixture of (a) an active macromolecular principle, (b) an aromatic alcohol absorption enhancer chosen from propyl gallate, butylated hydroxy toluene, butylated hydroxy anisole and analogues and derivatives thereof, wherein the aromatic alcohol absorption enhancer is present in an amount by weight greater than or equal to that of the active macromolecular principle, and (c) a solubilisation aid capable of increasing the solubility of the aromatic alcohol absorption enhancer in aqueous media.

14 Claims, No Drawings

FOREIGN PATENT DOCUMENTS

| WO | WO 0228436 | * | 4/2002 |
|---|---|---|---|
| WO | WO 03/022208 A2 | | 3/2003 |

OTHER PUBLICATIONS

International Search Report of PCT/GB2004/001651, mailed Aug. 30, 2004.
Database WPI, Section Ch, Week 198149, Derwent Publications Ltd., AN 1981-90325D, XP002292155.
Handbook of Pharmaceutical Excipients, Eds Wade & Weller, The Pharmaceutical Press, London UK, $2^{nd}$ edition, 1994.
Liu et al, "Cancer gene therapy targeting angiogenesis: An updated review", World J. Gastroenterol., 2006, 12, 6941-8.
Sutter et al, "Gene therapy for gastric cancer: is it promising?", World J. Gastroenterol., 2006, 12, 380-7.
"Dissociation Constants of Organic Acids and Bases", CRC Handbook of Chemistry and Physics $83^{rd}$ edition, 2002, pp. 8-49.
Sonnenberg & Kotchen, "New therapeutic approaches to reversing insulin resistance," Curr. Op. Neph. Hyperten., 1998, 7, 551-5.
Dressman et al, "In vitro-invivo correlations for lipophlic, poorly water-soluble drugs", European Journal of Pharmaceutical Sciences, 11 Suppl. 2 (2000) S73-S80.
May's Chemistry of Synthetic Drugs, pp. 12-16, $5^{th}$ edition, 1959.
Hidalgo et al, "Characterization of the Human Colon Carcinoma Cell Line (Caco-2) as a Model System . . . ", Gastroenterology 1989; 96:736-49.
Hilgers et al, "Caco-2 Cell Monolayers as a Model for Drug Transport Across the Intestinal Mucosa", Pharmaceutical Research, vol. 7, No. 9, 1990.
Sambuy et al, "The Caco-2 cell line as a model of the intestinal barrier: influence of cell and culture-related factors on Caco-2 cell functional characteristics", Cell Biology and Toxicology, 2005; 21: 1-26.
He et al, "Absorption of Ester Prodrugs in Caco-2 and Rat Intestine Models", Antimicrobial Agents and Chemotherapy, Jul. 2004, p. 2604-2609, vol. 48, No. 7.
Grasset et al, "Epithelial properties of human colonic carcinoma cell line Caco-2: electrical parameters", American Journal of Physiology, 1984, C260-C267.
Hirakata et al, "Adherence to and Penetration of Human Intestinal Caco-2 Epithelial Cell Monolayers of *Pseudomonas aeruginosa*", Infection and Immunity, Apr. 1998, pp. 1748-1751; vol. 66, No. 4.
The Merck Index, An Encyclopedia of Chemicals, Drugs, and Biologicals; $13^{th}$ Edition, 2001, pages: cover, 895, 896.
Growth Hormone from GenBank Accession No. NP-001075417, pp. 1-2, Accessed Jan. 29, 2009.
Growth Hormone from GenBank Accession No. CAA54461, pp. 1-2, Accessed Jan. 29, 2009.
Parathyroid Hormone from GenBank Accession No. AAA72730, pp. 1-2, Accessed Jan. 29, 2009.
STN Registry of Nov. 16, 1984.
Sigma "Products Information" extract for insulin, (Oct. 7, 1996).
Brange et al, "Chemical stability of insulin", Acta Pharm. Nord. 4(3); 149-158 (1992).
GenBank Accession No. CAA26189 for Calcitonin. Accessed Jul. 30, 2008.
GenBank Accession No. AAA49464 for growth hormone. Accessed Jul. 30, 2008.
Six pages of search results, Jul. 23, 2008.
Chang et al, J. Pharm. Pharmaceut Sci 7(1):8-12, (2004).
Atta et al, AAPS Pharm, Sci. Tech. 8(4):Article 106 (2007).
Ke et al, J. Pharm. Sci. 97(6):2208-16 (2008).
Extract from the Merck index (p. 480 and title page).
A US EPA report entitled "Alkylphenois Category (Section One)", (Apr. 19, 2006).
Alberts et al, Molecular Biology of the Cell, $4^{th}$ ed. Chapter 22, (2002). http://www.ncbi.nim.nih.gov/books/bv.fcgi?highlight=small%20intestine.pH&rid=mboc4.section.4113#4118, pp. 1-6.
International Search Report of PCT/GB2004/001650, mailed Sep. 28, 2004.
Van Hoogdalem et al., "Intestinal Drug Absorption Enhancement: An Overview", Pharmacology and Therapeutics, Elsevier, vol. 44, No. 3, 1989, pp. 407-443, XP002086283.
Aungst et al., "Enhancement of the Intestinal Absorption of Peptides and Non-peptides", Journal of Controlled Release, vol. 41, No. 1-2, 1996, pp. 19-31, XP004037568.
Dondeti et al., "In Vivo Evaluation of Spray Formulations of Human Insulin for Nasal Delivery", International Journal of Pharaceutics, vol. 122, No. 1-2, 1995, pp. 91-105, XP002295623.
Sasaici et al., "Effect of Ophtalmic Preservatives on Serum Concentration and Local Irritation of Ocularly Applied Insulin", Biological and Pharmaceutical Bulletin, vol. 18, No. 1, 1995, pp. 169-171, XP001183131.
Shen et al, "Pulmonary Delivery of Insulin: Absorption Enhancement of Insulin by Various Absorption Promoters in Rats", Journal of Chinese Pharmaceutical Sciences (2000), 9(1), 22-25.

\* cited by examiner

ABSORPTION ENHANCERS SUCH AS E.G. BHT, BHA OR PROPYL GALLATE

This application is the US national phase of international application PCT/GB2004/001650, filed 15 Apr. 2004, which designated the U.S. and claims priority of GB 0308732.7, filed 15 Apr. 2003, the entire contents of each of which are hereby incorporated by reference.

The present invention relates to the use of an aromatic alcohol to enhance the uptake of molecules, including biologically active macromolecules, into the body, suitably across the intestinal wall from the lumen of the gut. In particular the present invention relates to novel pharmaceutical compositions comprising an active macromolecular principle to be absorbed into the body, preferably across the intestinal wall.

Hydrophilic aromatic alcohols, in particular aromatic alcohols in which the hydroxy group is not attached directly to the aromatic nucleus, such as phenoxyethanol, phenyl ethanol and benzyl alcohol, have been employed in pharmaceutical practice for many years as solvents and plasticisers, and have a low toxicity profile when administered via various routes, including the. oral route. Those compounds are all liquids at room temperature, and can be readily dissolved in aqueous media.

Hydrophilic aromatic alcohols such as phenoxyethanol and related compounds including phenyl ethanol and benzyl alcohol, have a range of actions on intestinal cells, one of which is that, when present in relatively high local concentration, aromatic alcohols transiently increase the permeability of a barrier layer of intestinal cells.

It is postulated that this is due to the opening of the tight junctions between these cells creating pores through which even large molecules (macromolecules) can pass by diffusion.

Based on the finding that an increase in the permeability of a barrier layer of intestinal cells is only seen at relatively high local concentrations of hydrophilic aromatic alcohol, the applicant's research has shown that a solution of hydrophilic aromatic alcohol co-administered orally (as an elixir) with a detectable molecule produces no enhancement of uptake. It is postulated that this is because, before it reaches the absorption site (in the intestine), the hydrophilic alcohol is rapidly diluted in the gastrointestinal tract to a concentration below which it cannot exert its effect. In addition, the molecules whose uptake one is seeking to elicit will also be diluted out before the intestine is reached. It has now been found that another class of aromatic alcohols also displays characteristics of permeation enhancers. These compounds have hydroxyl groups attached directly to the aromatic nucleus and an additional substituent in the position para to the OH group, and typically display antioxidant properties, which may or may not be related to their ability to act as permeation enhancers. Examples of this class of compounds are propyl gallate, butylated hydroxy toluene (BHT) and butylated hydroxy anisole (BHA). Surprisingly, although these materials have been employed routinely in pharmaceutical practice for at least twenty years primarily in lipid-based formulations, generally as antioxidants, the observation that these materials are capable of acting as permeation enhancers has never been made. This is probably because these compounds are all solids which are sparingly soluble in water, thus making it difficult to incorporate them into water-based pharmaceutical formulations in high concentrations, and also preventing them from being available in soluble form to act as enhancers at elevated concentration when the formulation is dispersed in the lumen of the intestine, or close to any other mucosal surface where permeation enhancement is required.

The use of gallate esters or specifically propyl gallate has been described in U.S. Pat. No. 6,180,666 and U.S. Pat. No. 5,962,522 respectively as enhancers of bioavailability of small molecules via a mechanism in which the propyl gallate inhibits the activity of cytochrome P450 (in particular CY3PA, located in the endoplasmic reticulum), thereby reducing the metabolic degradation of small molecules on their passage through intestinal cells (known as the transcellular route). Propyl gallate and other esters of gallic acid appear to be potent inhibitors of cytochrome P450, and it is claimed that sufficient propyl gallate can be introduced into a formulation to exert a significant effect without the need for solubilisation aids. However, the enzyme inhibitor mechanism of action described for propyl gallate, however, cannot be expected to enhance the bioavailability of macromolecules, since macromolecules are incapable of entering unaided into intestinal cells, and so would not come into contact with the endoplasmic reticulum where the enzyme is located. Furthermore, macromolecules such as peptides and proteins are far less susceptible to the action of cytochrome P450 than are small drug molecules, so that degradation by this enzyme is not a major cause of the poor bioavailability of macromolecules from the gut, or other mucosal tissues. A much greater barrier is simply the size of the molecules themselves, which prevents them from entering into or passing through the cells lining mucosal tissues unaided, where cells which line these tissues form a continuous impassable wall.

It has now been found that, surprisingly, aromatic alcohols such as propyl gallate, BHT, BHA and analogues and derivatives thereof are capable of enhancing the passage of macromolecules across mucosal barriers by increasing the physical permeability of the mucosal cells. One possible mechanism for this to occur is by transient opening of the tight junctions in between these cells, creating channels along which the macromolecules can pass (paracellular route). An alternative mode of action is enhancement of fluid-phase pinocytosis, resulting in internalisation of bulk fluid together with macromolecules within vacuoles, which are transported from one side of the cell to the other. While yet other mechanisms still not clearly understood are also possible, it is considered unlikely that macromolecules actually gain direct access to the internal cytoplasmic compartment of the cells. It has been found that this phenomenon is concentration-dependent, and that provision of the aromatic permeation enhancer in the high concentrations increases the effect in vivo. Consequently, the use of solubilisation aids is advantageous for these compounds, particularly in the case of propyl gallate, to be able to enhance the bio-availability of macromolecules from mucosal tissues.

It has now also been discovered that there are certain agents, known here as solubilisation aids, which can be used to assist in solubilising these aromatic alcohol permeation enhancers, and which, furthermore, can increase their solubility, and/or rate of dissolution when exposed to aqueous media. This is clearly important if these materials are to exert their maximal effect as permeation enhancers.

The invention provides a pharmaceutical composition comprising a mixture of:
  (a) an active macromolecular principle; and
  (b) an aromatic alcohol absorption enhancer chosen from butylated hydroxy toluene, butylated hydroxy anisole and analogues and derivatives thereof, wherein the aromatic alcohol absorption enhancer is present in an amount by weight greater than or equal to that of the active macromolecular principle.

The invention further provides a pharmaceutical composition comprising a mixture of:

(a) an active macromolecular principle; and (b) an aromatic alcohol absorption enhancer chosen from propyl gallate, butylated hydroxy toluene, butylated hydroxy anisole and analogues and derivatives thereof, and (c) a solubilisation aid capable of increasing the solubility of the aromatic alcohol absorption anhancer in aqueous media, wherein the aromatic alcohol absorption enhancer is present in an amount by weight greater than or equal to that of the active macromolecular principle.

The invention also provides the use, in a pharmaceutical composition, of an aromatic alcohol chosen from butylated hydroxy toluene, butylated hydroxy anisole and analogues and derivatives thereof as an enhancer for the absorption of macromolecules into the body.

In a further embodiment the invention provides the use of an aromatic alcohol chosen from butylated hydroxy toluene, butylated hydroxy anisole and analogues and derivatives thereof in the manufacture of a medicament (pharmaceutical composition) containing an active macromolecular principle, in order to enhance absorption of the active macromolecular principle into the human or animal body.

The invention also provides the use, in a pharmaceutical composition, of an aromatic alcohol chosen from propyl gallate, butylated hydroxy toluene, butylated hydroxy anisole and analogues and derivatives thereof together with a solubilisation aid capable of increasing the solubility of the aromatic alcohol absorption enhancer in aqueous media as an enhancer for the absorption of macromolecules into the body.

In a further embodiment, the invention provides the use of an aromatic alcohol chosen from propyl gallate, butylated hydroxy toluene, butylated hydroxy anisole and analogues and derivatives thereof together with a solubilisation aid capable of increasing the solubility of the aromatic alcohol absorption enhancer in aqueous media in the manufacture of a medicament (pharmaceutical composition) containing an active macromolecular principle, in order to enhance absorption of the active macromolecular principle into the human or animal body.

The aromatic alcohol absorption enhancer may be propyl gallate or an analogue or a derivative thereof, and, preferably is propyl gallate. Suitable analogues and derivatives of propyl gallate include esters of gallic acid. The esters may be linear or branched chain $C_{1-12}$ alkyl, $C_{1-12}$ alkyloxy, $C_{1-12}$ alkylthio or $C_{2-12}$ alkenyl esters. The compounds are optionally substituted with halogen, linear or branched chain $C_{1-12}$ alkyl, $C_{1-12}$ alkyloxy, $C_{1-12}$ alkylthio or $C_{2-12}$ alkenyl esters. The aromatic alcohol absorption enhancer may also be chosen from BHT, BHA and analogues and derivatives thereof Suitable analogues and derivatives of BHT or BHA include analogues and derivatives of hydroxy toluene or hydroxy anisole where the methyl group or the methoxy group linked to the aromatic ring and/or the hydrogen ortho to the hydroxyl group are replaced by linear or branched chain $C_{1-12}$ alkyl, $C_{1-12}$ alkyloxy, $C_{1-12}$ alkylthio or $C_{2-12}$ alkenyl, either unsubstituted or substituted in any position, especially by halogen atoms. Preferably, the aromatic alcohol absorption enhancer is chosen from propyl gallate, BHT and BHA.

The aromatic alcohols disclosed above which are used in pharmaceutical practice as antioxidants are included at concentrations up to 0.1% w/v of the total formulation (see entries for individual compounds in the Handbook of Pharmaceutical Excipients, Eds Wade & Weller, The Pharmaceutical Press, London UK, $2^{nd}$ edition 1994). It is generally considered that higher concentrations of the compounds give no added antioxidant benefit, and it is thus standard pharmaceutical practice to restrict the concentration of the antioxidants in formulations to no greater than 0.1%. When used as absorption enhancers according to the present invention, however, the efficacy of these compounds is concentration dependent up to a much higher level, and their proportions in a pharmaceutical formulation are much higher than previously described in the prior art.

To the applicant's knowledge, there is no suggestion in the prior art of the use of these agents as antioxidants in pharmaceutical formulations. None of these agents play any role in enhancing absorption of macromolecules by the oral route, or that these agents may be included in formulations at levels higher than is standard pharmaceutical practice for antioxidants.

For example, EP-A-0295941 discloses a formulation for oral administration in which BHA, BHT or PG may optionally be included, so that it is clear that their presence is not essential for biological efficacy of the formulation. No concentrations of these agents are specified, and the formulation is intended as a controlled-release dosage form, in marked contrast to the present invention where immediate dissolution is desirable to ensure rapid release from the capsule.

WO-A-0222158 provides compositions comprising cyclosporin (not a macromolecule) and containing BHA, BHT and PG generally as antioxidants. Although no specific concentrations of the antioxidants are given, the use of the compounds as antioxidants suggests a level of no greater than 0.1% wt.

U.S. Pat. No. 5,756,450 discloses compositions comprising low molecular water insoluble compounds including water insoluble polypeptides, especially cyclopeptides such as the cyclosporins. BHA or BHT may be included as antioxidants, again in very small quantities.

U.S. Pat. No. 5,342,625 again discloses compositions comprising cyclosporins. A solubilisation aid may be present to help form a microemulsion pre-concentrate of the cyclosporin. BHA or BHT may be present at low levels as antioxidants.

BHA and BHT may also be present as antioxidants in the compositions of U.S. Pat. No. 3,996,355 which comprise any drug which is stable in the presence of a vegetable oil vehicle, more specifically water-sensitive drugs having a bitter taste. Macromolecules are not envisaged.

Suitable solubilisation aids include, but are not limited to, bile acids or salts such as sodium taurocholate or taurodeoxycholate, benzyl alcohol, phenyl ethanol, phenoxyethanol, transcutol or isopropanol.

The active macromolecular principles falling within the scope of the invention include all molecules capable of having a beneficial effect when absorbed into the human or animal body, especially through the intestinal wall. The beneficial effect may be, for example, therapeutic, cosmetic or preventative such as prophylactic or contraceptive. The active macromolecular principles can be of natural (biological), synthetic or semi-synthetic origin.

Macromolecules are preferably defined as molecules having a molecular weight of over 1000 Da, preferably over 2000 Da and most preferably over 3000 Da. Examples of macromolecules, including macromolecular active macromolecular principles, include:

1. Polypeptides and proteins such as insulin; calcitonin; human serum albumin; growth hormone; growth hormone releasing factors; galanin; parathyroid hormone; blood clotting proteins such as kinogen, prothombin, fibrinogen, Factor VII, Factor VIII of Factor IX; erythropoeitins and EPO mimetics; colony stimulating factors including GCSF and GMCSF; platelet-derived growth factors; epidermal growth factors; fibroblast growth factors; transforming growth factors; GLP-1; GAG; cytokines; insulin-like growth factors; bone- and cartilage-inducing factors; neurotrophic factors; interleukins including IL-1, IL-2, IL-3, IL-4, IL-5, IL-6, IL-7, IL-8, IL-9, IL-10, IL-11, IL-12; interferons including interferon gamma, interferon-1a, interferon alphas; TNF alpha;

TNF beta; TGF-beta; cholera toxin A and B fragments; *E. coli* enterotoxin A and B fragments; secretin; enzymes including histone deacetylase, superoxide dismutase, catalase, adenosine deaminase, thymidine kinase, cytosine deaminase, proteases, lipases, carbohydrases, nucleotidases, polymerases, kinases and phosphatases; transport or binding proteins especially those which bind and/or transport a vitamin, metal ion, amino acid or lipid or lipoprotein such as cholesterol ester transfer protein, phospholipid transfer protein, HDL binding protein; connective tissue proteins such as a collagen, elastin or fibronectin; a muscle protein such as actin, myosin, dystrophin, or mini-dystrophin; a neuronal, liver, cardiac, or adipocyte protein; a cytotoxic protein; a cytochrome; a protein which is able to cause replication, growth or differentiation of cells; a signalling molecule such as an intra-cellular signalling protein or an extracellular signalling protein (eg hormone); trophic factors such as BDNF, CNTF, NGF, IGF, GMF, aFGF, bFGF, VEGF, NT3, T3 and HARP; apolipoproteins; antibody molecules; receptors in soluble form such as T-cell receptors and receptors for cytokines, interferons or chemokines; proteins or peptides containing antigenic epitopes and fragments; and derivatives, conjugates and sequence variants of any of the above. These and other proteins may be derived from human, plant, animal, bacterial or fungal sources, and extracted either from natural sources, prepared as recombinants by fermentation or chemically synthesised.

2. Polynucleotides such as long-chain linear or circular single-, double- or triple-stranded DNA, single-, double- or triple-stranded RNA, oligonucleotides such as antisense DNA or RNA, and analogues thereof including PNA and phosphothioate derivates. In one embodiment it is preferred that the polynucleotides used in the invention contain a CpG motif. The coding sequence of the polynucleotide may encode a therapeutic product, in particular the coding sequence may encode an extracellular protein (e.g. a secreted protein); an intracellular protein (e.g. cytosolic, nuclear or membrane protein); a protein present in the cell membrane; a blood protein, such as a clotting protein (e.g. kinogen, prothrombin, fibrinogen factor VII, factor VIII or factor IX); an enzyme, such as a catabolic, anabolic gastro-intestinal, metabolic (e.g. glycolysis or Krebs cycle), or a cell signalling enzyme, an enzyme which breaks down or modifies lipids, fatty acids, glycogen, amino acids, proteins, nucleotides, polynucleotides (e.g. DNA or RNA) or carbohydrate (e.g. protease, lipase or carbohydrase), or a protein modifying enzyme, such as an enzyme that adds or takes chemical moieties from a protein (e.g. a kinase or phosphatase); a transport or binding protein (e.g. which binds and/or transports a vitamin, metal ion, amino acid or lipid, such as cholesterol ester transfer protein, phospholipid transfer protein or an HDL binding protein); a connective tissue protein (e.g. a collagen, elastin or fibronectin); a muscle protein (e.g. actin, myosin, dystrophin or mini-dystrophin); a neuronal, liver, cardiac or adipocyte protein; a cytotoxic protein; a cytochrome; a protein which is able to cause the replication, growth or differentiation of cells; a protein which aids transcription or translation of a gene or regulates transcription or translation (e.g. a transcription factor or a protein that binds a transcription factor or polymerase); a signalling molecule, such as an intracellular or extracellular signalling molecule (e.g. a hormone); an immune system protein such as an antibody, T cell receptor, MHC molecule, cytokine (e.g IL-1, IL-2, IL-3, IL-4, IL-5, IL-6, IL-7, IL-8, IL-9, IL-10, TNF-, TNF-, TGF-), an interferon (e.g. IFN-, IFN-, IFN-), chemokine (e.g. MIP-1, MIP-1, RANTES), an immune receptor (e.g. a receptor for a cytokine, interferon or chemokine, such as a receptor for any of the above-mentioned cytokines, interferons or chemokines) or a cell surface marker (e.g. macrophage, T cell, B cell, NK cell or dendritic cell surfacemarker)(eg. CD 1, 2, 3, 4, 5, 6, 7, 8, 16, 18, 19, 28, 40, or 45; or a natural ligand thereof), a trophic factor (e.g. BDNF, CNTF, NGF, IGF, GMF, aFGF, bFGF, VEGF, NT3, T5, HARP) or an apolipoprotein; a tumour suppressor (e.g. p53, Rb, Rap1A, DCC or k-rev); a suicide protein (thymidine kinase or cytosine deaminase); or a gene repressor. The proteins and peptides encoded by the polynucleotides useful in the invention may be immunogenic i.e. contain an antigen specific to the activity of the protein against which antibodies are generated by the immune system.

The polynucleotide may have control sequences operably linked to the coding sequence. The control sequences may typically be those of any eukaryote or of a virus which infects such eukaryotes. The polynucleotide may comprise an origin of replication.

The polynucleotides may be chemically modified. This may enhance their resistance to nucleases or may enhance their ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates. Alternatively mixed backbone oligonucleotides (MBOs) may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloligoribonucleotides.

The polynucleotide suitable for use in the invention is preferably in a form in which it is substantially free of or associated with cells or with cellular, prokaryotic, eukaryotic, nuclear, chromatin, histone or protein material. It may be in substantially isolated form, or it may be in substantially purified form, in which case it will generally comprise more than 90%, e.g. (more than or at least) 95%, 98% or 99% of the polynucleotide or dry mass in the preparation. Thus the polynucleotide may be in the form of 'naked DNA'.

3. Polysaccharides such as heparin, low-molecular weight heparin, polymannose, cyclodextrins and lipopolysaccharide.

4. Any or all of the above either separately or in combination with each other (for example in the form of a heteroconjugate), or with additional agents.

In preferred embodiments of the invention the active macromolecular principle to be absorbed is selected from calcitonin, insulin, low molecular weight heparin, erythropoeitin, human growth hormone and parathyroid hormone, particularly calcitonin, insulin and parathyroid hormone.

Depending on the nature of additional excipients employed, the pharmaceutical composition of the invention may be in liquid, solid, semi-solid or gel form. The pharmaceutical composition of the invention is suitable for administration via any route giving access to different mucosal tissues such as buccal and sublingual mucosa, the nasal palate, the lungs, the rectum, the intestinal tract (including the large and small intestines) and the vagina. In the case of liquid, semi-solid or gel formulations, these may be either anhydrous or aqueous.

Where the intended site of action of the composition of the invention is the intestine, it is desirable that the composition is enclosed within an enteric coating which can withstand the stomach, so that the components of the formulation remain together, undiluted and in close association until they reach the tissues of the small intestine or colon. Such formulations will suitably be anhydrous. Compositions in liquid form will suitably be administered as enteric-coated capsules, while solid formulations may be administered either within enteric-coated capsules, or in tablet form, preferably as enteric-coated tablets.

The enteric coating is chosen appropriately to withstand the natural condition of the stomach and to become permeable at the desired location in the intestine. This is preferably determined by the pH conditions which modulate along the length of the intestine. Where the site of action is the small intestine, it is preferred that the enteric coating becomes permeable and releases its contents at a pH from 3 to 7, preferably from 5.5 to 7, more preferably from 5.5 to 6.5. Where the intended site of action is the colon, it is preferred that the enteric coating becomes permeable and releases its contents at a pH of 6.8 or above.

Suitable enteric coatings are well known in the art and include cellulose acetate, phthalate, shellac and polymethacrylates such as those selected from the L and S series of Eudragits in particular Eudragits L12.5P, L12.5, L100, L100-55, L30 D-55, S12.5P, S12.5 and S100. Suitable plasticisers or wetting agents, such as triethyl citrate and polysorbate 80 may also be included in the coating mixture.

Selection of an appropriate coating for the capsule, which is preferably an HPMC or gelatine capsule, can readily be made by the person skilled in the art based on their knowledge and the available literature supporting the Eudragit products.

Where the intended site of action is the nasal mucosa, the formulation may be in the form of an aqueous solution or as a dry powder, which can be administered as a spray.

Where the intended site of action is the rectum, an appropriate method of administration is as an anhydrous liquid or solid enclosed within a capsular shell, or incorporated into the matrix of an erodible suppository.

For vaginal application, adminstration of the formulation in gel form is also appropriate.

The aromatic alcohol absorption enhancers are preferably water-insoluble. The enhancer is suitably present in the composition in an amount of from 1 to 40% by weight, preferably from 5 to 35% by weight, more preferably from 10 to 30% by weight.

In the compositions of the invention, the aromatic alcohol absorption enhancer is present in an amount (by weight) greater than or equal to that of the active macromolecular principle. This provides an effective concentration of aromatic alcohol absorption enhancer at the intestinal cell barrier layer (intestinal wall) so as to cause enhanced absorption in the co-presence of a suitable amount of the active macromolecular principle which, when absorbed, will exert its normal beneficial effect. The practitioner of the invention would select the amounts of the aromatic alcohol absorption enhancer and active macromolecular principle on the basis of the amount (for example, blood concentration level) of the active macromolecular principle concerned which is necessary for therapeutic efficacy. The weight ratio of aromatic alcohol absorption enhancer to active macromolecular principle in the mixture contained in the capsule is suitably at least 1:1, preferably at least 5:1, for example from 1:1 to 100:1, preferably from 3:1 to 50:1, most preferably from 5:1 to 20:1.

The ratio of solubilisation aid to aromatic alcohol absorption enhancer is suitably at least 1:1, preferably from 1:1 to 10:1, and most preferably from 1.5:1 to 5:1.

The absolute amount of the active macromolecular principle would be selected on the basis of the dosage of the substance required to exert the normal beneficial effect with respect to the dosage regimen used and the patient concerned. Determination of these amounts falls within the mantle of the practitioner of the invention.

In the composition for oral administration it is preferred that the contents of the capsule comprises a suitable amount of the active macromolecular principle to achieve its normal therapeutic effect. For example, the composition may contain from 0.05 to 50%, preferably from 0.1 to 25%, more preferably from 0.1 to 10% by weight of the active macromolecular principle based on the weight of the capsule contents (not including the capsule itself).

The composition of the invention may further comprise one or more other absorption enhancer compounds, for example, medium chain fatty acids and medium chain monoglycerides.

The composition of the invention may optionally further comprise any conventional additive used in the formulation of pharmaceutical products including, for example, anti-oxidants, anti-microbials, suspending agents, fillers, diluents, absorbents, glidants, binders, anti-caking agents, lubricants, disintegrants, swelling agents, viscosity regulators, plasticisers and acidity regulators (particularly those adjusting the intestinal milieu to between 7 and 7.5). Suitable swelling agents include sodium starch glycolate, pregelatinised starch, microcrystalline cellulose, crosprovidone and magnesium aluminium silicate or mixtures thereof Sodium starch glycolate and other polyaccharide-based swelling agents may be included in an amount of from 5 to 10% by weight. Crosprovidone may be included in an amount of from 5 to 30% by weight.

The composition of the invention may optionally further comprise additional active principles which may enhance the desired action of the composition in a synergistic fashion. For example, where the active macromolecular principle is insulin, the composition may also comprise an insulin sensitiser capable of increasing the body's response to the insulin absorbed. Examples of sensitisers which could be employed in this fashion are troglitazone, pioglitazone, rosiglitazone and other members of the glitazone class of molecules.

In the composition of the invention where the mixture is contained in a capsule or tablet which comprises the aromatic alcohol absorption enhancer and active macromolecular principle, the formulation is preferably substantially anhydrous. In more preferred embodiments of the invention the entire composition is substantially anhydrous. Substantially anhydrous in the context of this invention means less than 5%, preferably less than 1% and more preferably less than 0.5% water by weight of the mixture.

The compositions of the invention can, depending on the active macromolecular principle used therein, be used in the treatment of a variety of conditions and diseases of the human or animal body by therapy or, alternately, can be used to introduce macromolecules essential for the diagnosis of diseases and conditions within the human or animal body. The compositions of the invention are preferably pharmaceutical or cosmetic compositions.

In the compositions of the invention the mixture contained in the capsule may be a liquid, semi-solid or gel, which is either in the form of a solution or a microparticulate dispersion. That is to say the active macromolecular principle(s) for absorption are incorporated into the formulation either in the form of a solution or as a microparticulate dispersion. Alternatively, the composition may be in the form of a solid.

The compositions of the invention are suitably produced by preparing a substantially anhydrous mixture of the active macromolecular principle and the aromatic alcohol absorption enhancer and then optionally filling uncoated capsules with the mixture and optionally coating them with an appropriate polymer mixture to achieve the desired permeability properties.

The following Examples serve to illustrate the present invention and should not be construed as limiting.

EXAMPLES

Example 1

Effect in Permeabilising Cell Culture Monolayer

Caco-2 cells (a cell line derived from human colon adenocarcinoma) are grown as a confluent mono-layer on the surface of a porous membrane (pore size 0.4 µm, surface area 0.33 cm$^2$) separating two aqueous compartments, the upper compartment filled with 200 µl of culture medium, and the lower compartment containing 600 µl of the culture medium. Electrical resistance across the mono-layer is measured using an epithelial voltohmeter connected to electrodes inserted into the medium on either side of the mono-layer in the upper and lower compartments. This trans-epithelial electrical resistance (TEER) is measured immediately before, and fifteen minutes after the addition of aromatic alcohols to the upper compartment (typical results are given in the table below). Four replicates are employed for each compound, whose concentrations are shown in the table below. Fall in TEER is considered indicative of the increased flow of materials (including bulk fluid phase) across the cell monolayer.

Falls of greater than 50% of the initial value are considered significant. Reducing the concentration tends to reduce the effect observed.

TABLE

| Agent | Concentration (mg/ml) | TEER (ohm · cm$^2$) Before addition | 15 minutes after addition |
|---|---|---|---|
| Propyl gallate | 13 | 494 | −0.6 |
| Propyl gallate | 0.2 | 667 | 629 |
| Butylated hydroxy anisole | 0.3 | 564 | 183 |
| Butylated hydroxy toluene | 0.3 | 633 | 194 |

Example 2

Preparation of Formulation Containing Insulin, Propyl Gallate and Sodium Taurocholate Sodium taurocholate in an amount of 150 mg is mixed with 75 mg of propyl gallate in a glass vial and 825 µl of distilled water are added. Dissolution at room temperature is not achieved even on prolonged shaking, but after warming with brief sonication in an ultrasonic bath a clear colourless solution is obtained. Bovine insulin in an amount of 8.4 mg is added to the solution with mixing, followed by 10 µl of glacial acetic acid while vortexing the insulin suspension. A clear solution is rapidly obtained, with a pH of 3.15. The contents of the vial are frozen rapidly with shaking and lyophilised overnight. The following day a dry solid is obtained. An amount of 10 mg of the solid is weighed into a 2 ml vial and 50 µl of distilled water added. A clear solution forms rapidly.

Example 3

Preparation of Formulation Containing Insulin, Propyl Gallate and Sodium Taurodeoxycholate Identical conditions to those described in example 2 are employed using taurodeoxycholate instead of taurocholate. The pH of the final solution before drying is 3.36. A clear solution forms rapidly on addition of distilled water to the dried solid as before.

Example 4

Preparation of Formulation Containing Calcitonin, Propyl Gallate and Sodium Taurocholate Identical conditions to those described in example 2 are employed, except that 2.3 mg of salmon calcitonin is dissolved in distilled water, and the entire solution added to the mixture of sodium taurocholate and propyl gallate. A clear solution forms rapidly on addition of distilled water as before.

Example 5

Preparation of Formulation Containing Calcitonin, Propyl Gallate and Sodium Taurodeoxycholate Identical conditions to those described in example 4 are employed, except that taurodeoxycholate is employed instead of taurocholate.

Example 6

Preparation of Formulation Containing Parathyroid Hormone, Propyl Gallate and Sodium Taurocholate Identical conditions to those described in example 4 are employed, except that 0.5 mg parathyroid hormone is employed instead of calcitonin.

Example 7

Preparation of Formulation Containing Parathyroid Hormone, Propyl Gallate and Sodium Taurodeoxycholate Identical conditions to those described in example 6 are employed, except that taurodeoxycholate is employed instead of taurocholate.

Example 8

Preparation of Formulation Containing Parathyroid Hormone, Propyl Gallate and Sodium Taurodeoxycholate Identical conditions to those described in example 7 are employed, except that the bile salt/PG mixture is dried without addition of protein, and parathyroid hormone is added as a dry powder to the dry residue after lyophilisation.

Example 9

Preparation of Formulation Containing Human Growth Hormone, Propyl Gallate and Sodium Taurodeoxycholate Identical conditions to those described in example 8 are employed, except that 20 mg of human growth hormone is employed instead of parathyroid hormone.

Example 10

Preparation of Formulation Containing Calcitonin, Propyl Gallate and Propylene Glycol 75 mg of propyl gallate is dissolved by vortexing in 200 µl propylene glycol. 200 µl of the resultant solution is then transferred to a vial containing 1 mg of solid calcitonin. The vial is vortexed briefly to disperse the solid, then shaken for one hour at 37° C., giving a clear solution.

Example 10

Preparation of Formulation Containing Calcitonin, Propyl Gallate and Benzyl Alcohol 100 mg of propyl gallate is vortexed in 200 μl of benzyl alcohol, giving a clear solution after several minutes at room temperature. 200 μl of the resultant solution is then transferred to a vial containing 1 mg of solid calcitonin. The vial is vortexed briefly to disperse the solid.

Example 11

Preparation of Formulation Containing Calcitonin, Propyl Gallate and Transcutol 100 mg of propyl gallate is vortexed in 200 μl of transcutol, giving a clear solution after one minute at room temperature. 200 μl of the resultant solution is then transferred to a vial containing 1 mg of solid calcitonin. The vial is vortexed briefly to disperse the solid for one hour at 37° C., giving a clear solution. 200 μl of the resultant solution is then transferred to a vial containing 1 mg of solid calcitonin. The vial is vortexed briefly to disperse the solid, then shaken for one hour at 37° C., giving a clear solution. 100 μl of the solution is transferred to a fresh vial to which 100 μl of distilled water is added. All components remain in solution as a single-phase clear liquid.

Example 12

Preparation of Formulation Containing Calcitonin, Butylated Hydroxytoluene and Transcutol 100 mg of butylated hydroxy toluene is vortexed in 200 μl of transcutol, giving a clear solution after several minutes at room temperature. 200 μl of the resultant solution is then transferred to a vial containing 1 mg of solid calcitonin. The vial is vortexed briefly to disperse the solid, then shaken for one hour at 37° C., giving a clear solution. 100 μl of the solution is transferred to a fresh vial to which 100 μl of distilled water is added, giving a clear opalescent solution at 37° C.

The invention claimed is:

1. A method of enhancing the absorption of an active macromolecular principle which is a polypeptide or protein, polynucleotide or polysaccharide in a patient, which method comprises orally administering to said patient a composition comprising an aromatic alcohol absorption enhancer chosen from propyl gallate, butylated hydroxy toluene (BHT), butylated hydroxy anisole (BHA) and analogues and derivatives thereof, wherein the aromatic alcohol absorption enhancer is present in an amount by weight greater than or equal to that of the active macromolecular principle, wherein the composition is coated with an enteric coating which becomes permeable at a pH of from 3 to 7, and wherein when the aromatic alcohol is propyl gallate or an analogue or derivative thereof, the composition further comprises a solubilization aid capable of increasing the solubility of the aromatic alcohol absorption enhancer in aqueous media.

2. A method according to claim 1, wherein the composition enhances the absorption of the active macromolecular principle across the intestinal wall.

3. A method of enhancing the absorption of an active macromolecular principle which is a polypeptide or protein, polynucleotide or polysaccharide in a patient, which method comprises orally administering to said patient an aromatic alcohol chosen from propyl gallate, butylated hydroxy toulene, butylated hydroxy anisole and analogues and derivatives thereof together with a solubilization aid capable of increasing the solubility of the aromatic alcohol absorption enhancer in aqueous media.

4. A method according to claim 2, wherein the composition comprises less than 5% by weight of water.

5. A method according to claim 2, wherein the solubilization aid is selected from a conjugated bile acid or salt, benzylalcohol, phenylethanol, phenoxyethanol, transcutol and isopropanol.

6. A method according to claim 2, wherein the composition is comprised in a medicament, which medicament is provided in the form of a solution, as a microparticulate dispersion or as a solid.

7. A method according to claim 2, wherein the active macromolecular principle is a polypeptide or protein.

8. A method according to claim 7, wherein the active macromolecular principle is insulin, calcitonin, growth hormone, parathyroid hormone, erythropoeitin, GLP1 or GCSF, or a derivative or analogue thereof, either synthetic or from natural sources, conforming to structures derived from either human or animal origin.

9. A method according to claim 8, wherein the active macromolecular principle is insulin, calcitonin, parathyroid hormone or a derivative or analogue thereof, either synthetic or from natural sources, conforming to structures derived from either human or animal origin.

10. A method according to claim 9, wherein the active macromolecular principle is insulin or a derivative or an analogue thereof, either synthetic or from natural sources, conforming to structures derived from either human or animal origin and an insulin sensitizing agent is also present.

11. A method according to claim 2, wherein the active macromolecular principle is a polynucleotide which is single, double or triple-stranded RNA or a polysaccharide which is heparin.

12. A method according to claim 11, wherein the polynucleotide is double-stranded RNA.

13. A method according to claim 1, wherein the active macromolecular principle has a molecular weight of over 2000 Da.

14. A method according to claim 1, wherein the active macromolecular principle has a molecular weight of over 3000 Da.

* * * * *